(12) United States Patent
Tan et al.

(10) Patent No.: US 8,282,605 B2
(45) Date of Patent: *Oct. 9, 2012

(54) FLASHBACK BLOOD COLLECTION NEEDLE

(75) Inventors: Chee Leong Alvin Tan, Singapore (SG); Stanley Sim, Singapore (SG); Jon Moh, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/824,818

(22) Filed: Jun. 28, 2010

(65) Prior Publication Data

US 2010/0262038 A1   Oct. 14, 2010

Related U.S. Application Data

(62) Division of application No. 12/044,354, filed on Mar. 7, 2008, now Pat. No. 7,766,879.

(51) Int. Cl.
*A61M 5/178* (2006.01)

(52) U.S. Cl. .................................. 604/168.01

(58) Field of Classification Search ............. 604/168.01, 604/900

See application file for complete search history.

(56) References Cited

U.S. PATENT DOCUMENTS

| | | | |
|---|---|---|---|
| 4,106,497 A | 8/1978 | Percarpio | |
| 4,207,870 A * | 6/1980 | Eldridge | 600/579 |
| 4,305,406 A | 12/1981 | Megahed | |
| 4,572,210 A * | 2/1986 | McKinnon | 600/578 |
| 4,573,976 A | 3/1986 | Sampson et al. | |
| 4,641,663 A | 2/1987 | Juhn | |
| 4,795,443 A | 1/1989 | Permenter et al. | |
| 4,840,619 A | 6/1989 | Hughes | |
| 4,894,055 A | 1/1990 | Sudnak | |
| 4,900,307 A | 2/1990 | Kulli | |
| 4,994,046 A | 2/1991 | Wesson et al. | |
| 5,015,241 A | 5/1991 | Feimer | |
| 5,195,985 A | 3/1993 | Hall | |
| 5,215,534 A | 6/1993 | DeHarde et al. | |
| 5,222,502 A | 6/1993 | Kurose | |
| 5,242,417 A | 9/1993 | Paudler | |
| 5,256,153 A | 10/1993 | Hake | |
| 5,295,970 A | 3/1994 | Clinton et al. | |
| 5,303,713 A | 4/1994 | Kurose | |
| 5,312,372 A | 5/1994 | DeHarde et al. | |
| 5,336,199 A | 8/1994 | Castillo et al. | |

(Continued)

FOREIGN PATENT DOCUMENTS

EP    1579805 A1    9/2005

(Continued)

*Primary Examiner* — Nicholas Lucchesi
*Assistant Examiner* — Diva K Chander
(74) *Attorney, Agent, or Firm* — The Webb Law Firm

(57) ABSTRACT

A needle assembly includes a transparent or translucent housing with a fluid inlet end, a fluid outlet end, a flashback chamber, and a venting mechanism therebetween. Substantially axially aligned inlet and outlet cannulas extend from the housing and communicate with the chamber. A sealable sleeve covers the external end of the outlet cannula. Relative volumes of the cannulas, the chamber, and the sleeve are selected to provide rapid reliable flashback indicative of venous entry with an internal vent positioned within the housing so as to divide the interior into first and second chambers, with the second chamber being adapted to maintain a negative pressure therein relative to the external environment so as to inhibit leakage of blood from the needle on withdrawal from the patient.

14 Claims, 12 Drawing Sheets

U.S. PATENT DOCUMENTS

| | | | |
|---|---|---|---|
| 5,348,544 A | 9/1994 | Sweeney et al. | |
| 5,356,392 A | 10/1994 | Firth et al. | |
| 5,411,492 A | 5/1995 | Sturman et al. | |
| 5,439,449 A | 8/1995 | Mapes et al. | |
| 5,466,223 A | 11/1995 | Bressler et al. | |
| 5,501,675 A | 3/1996 | Erskine | |
| 5,542,932 A | 8/1996 | Daugherty | |
| 5,672,161 A | 9/1997 | Allen et al. | |
| 5,676,658 A | 10/1997 | Erskine | |
| 5,702,369 A | 12/1997 | Mercereau | |
| 5,704,920 A | 1/1998 | Gyure | |
| 5,755,522 A | 5/1998 | Ito | |
| 5,984,899 A | 11/1999 | D'Alessio et al. | |
| D422,700 S | 4/2000 | Crawford et al. | |
| 6,149,629 A | 11/2000 | Wilson et al. | |
| D442,280 S | 5/2001 | Crawford et al. | |
| 6,261,263 B1 | 7/2001 | Huet et al. | |
| 6,298,541 B1 | 10/2001 | Newby et al. | |
| 6,436,086 B1 | 8/2002 | Newby et al. | |
| 6,440,104 B1 | 8/2002 | Newby et al. | |
| 6,524,277 B1 * | 2/2003 | Chang | 604/164.02 |
| 6,533,760 B2 * | 3/2003 | Leong | 604/168.01 |
| 6,592,556 B1 | 7/2003 | Thorne | |
| 6,623,456 B1 | 9/2003 | Holdaway et al. | |
| 6,635,032 B2 | 10/2003 | Ward, Jr. | |
| 6,648,855 B2 | 11/2003 | Crawford et al. | |
| 6,699,217 B2 | 3/2004 | Bennett et al. | |
| 6,712,792 B2 * | 3/2004 | Leong | 604/168.01 |
| 6,780,169 B2 | 8/2004 | Crawford | |
| 6,837,877 B2 | 1/2005 | Zurcher | |
| 6,869,415 B2 | 3/2005 | Asbaghi | |
| 6,984,223 B2 | 1/2006 | Newby et al. | |
| 7,001,363 B2 | 2/2006 | Ferguson et al. | |
| 7,128,726 B2 | 10/2006 | Crawford et al. | |
| 7,147,624 B2 | 12/2006 | Hirsiger et al. | |
| 7,160,267 B2 | 1/2007 | Brown | |
| 7,163,526 B2 | 1/2007 | Leong et al. | |
| 7,223,258 B2 | 5/2007 | Crawford | |
| 7,226,432 B2 | 6/2007 | Brown | |
| 7,396,343 B2 | 7/2008 | Brown | |
| 7,428,773 B2 | 9/2008 | Newby et al. | |
| D604,836 S | 11/2009 | Crawford et al. | |
| D604,837 S | 11/2009 | Crawford et al. | |
| D604,838 S | 11/2009 | Crawford et al. | |
| D604,839 S | 11/2009 | Crawford et al. | |
| D605,287 S | 12/2009 | Crawford et al. | |
| 7,766,879 B2 * | 8/2010 | Tan et al. | 604/168.01 |
| 2002/0193748 A1 | 12/2002 | Cocker et al. | |
| 2003/0105414 A1 | 6/2003 | Leong | |
| 2003/0229315 A1 | 12/2003 | Leong et al. | |
| 2004/0059302 A1 | 3/2004 | Crawford et al. | |
| 2004/0092872 A1 | 5/2004 | Botich et al. | |
| 2005/0004524 A1 | 1/2005 | Newby et al. | |
| 2005/0187493 A1 | 8/2005 | Swenson et al. | |
| 2005/0245868 A1 | 11/2005 | Brown | |
| 2005/0245869 A1 | 11/2005 | Brown | |
| 2005/0245870 A1 | 11/2005 | Brown | |
| 2005/0245885 A1 | 11/2005 | Brown | |
| 2006/0036219 A1 | 2/2006 | Alvin | |
| 2007/0106220 A1 | 5/2007 | Brown | |
| 2007/0167914 A1 | 7/2007 | Leong et al. | |
| 2008/0086085 A1 | 4/2008 | Brown | |
| 2008/0177202 A1 | 7/2008 | Brown | |
| 2008/0319345 A1 | 12/2008 | Swenson | |
| 2008/0319346 A1 | 12/2008 | Crawford et al. | |
| 2009/0204026 A1 | 8/2009 | Crawford et al. | |
| 2009/0227896 A1 | 9/2009 | Tan et al. | |

FOREIGN PATENT DOCUMENTS

| | | |
|---|---|---|
| EP | 1665986 B1 | 6/2009 |
| WO | 9629107 A1 | 9/1996 |
| WO | 2006022716 A1 | 3/2006 |

* cited by examiner

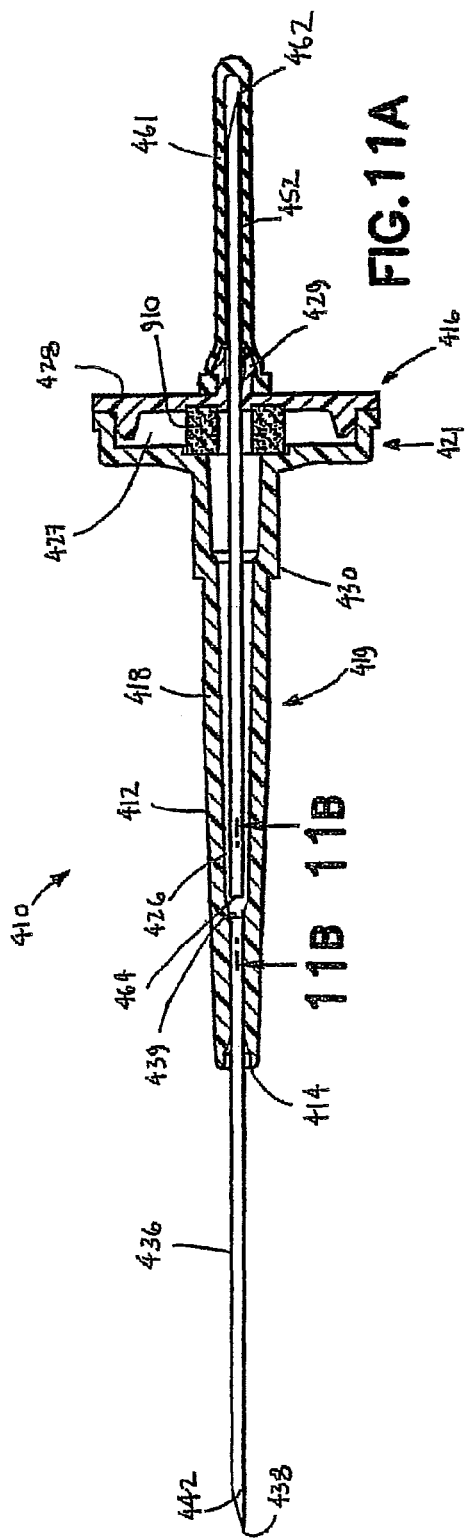
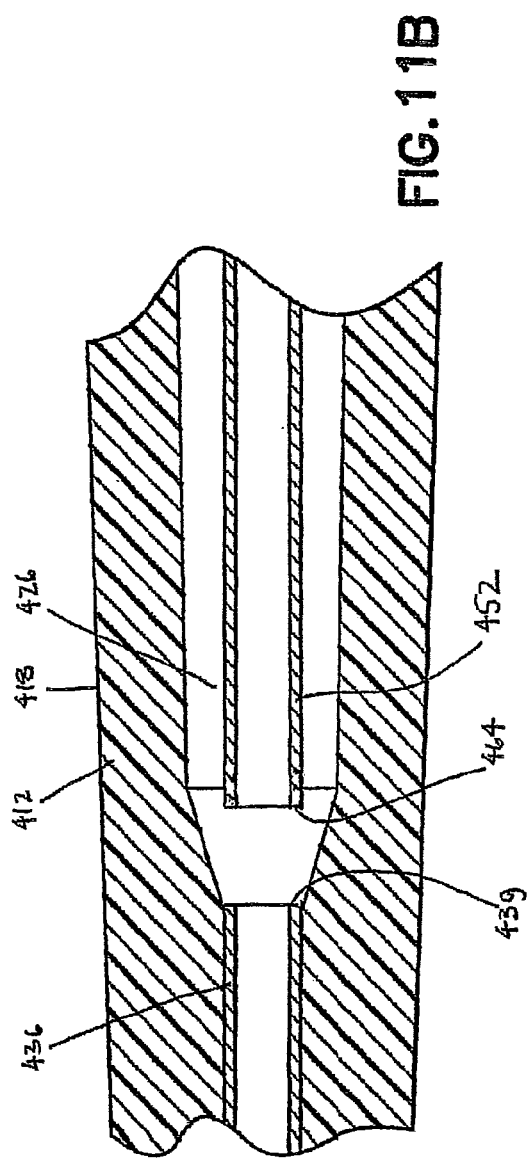
FIG. 11A
FIG. 11B

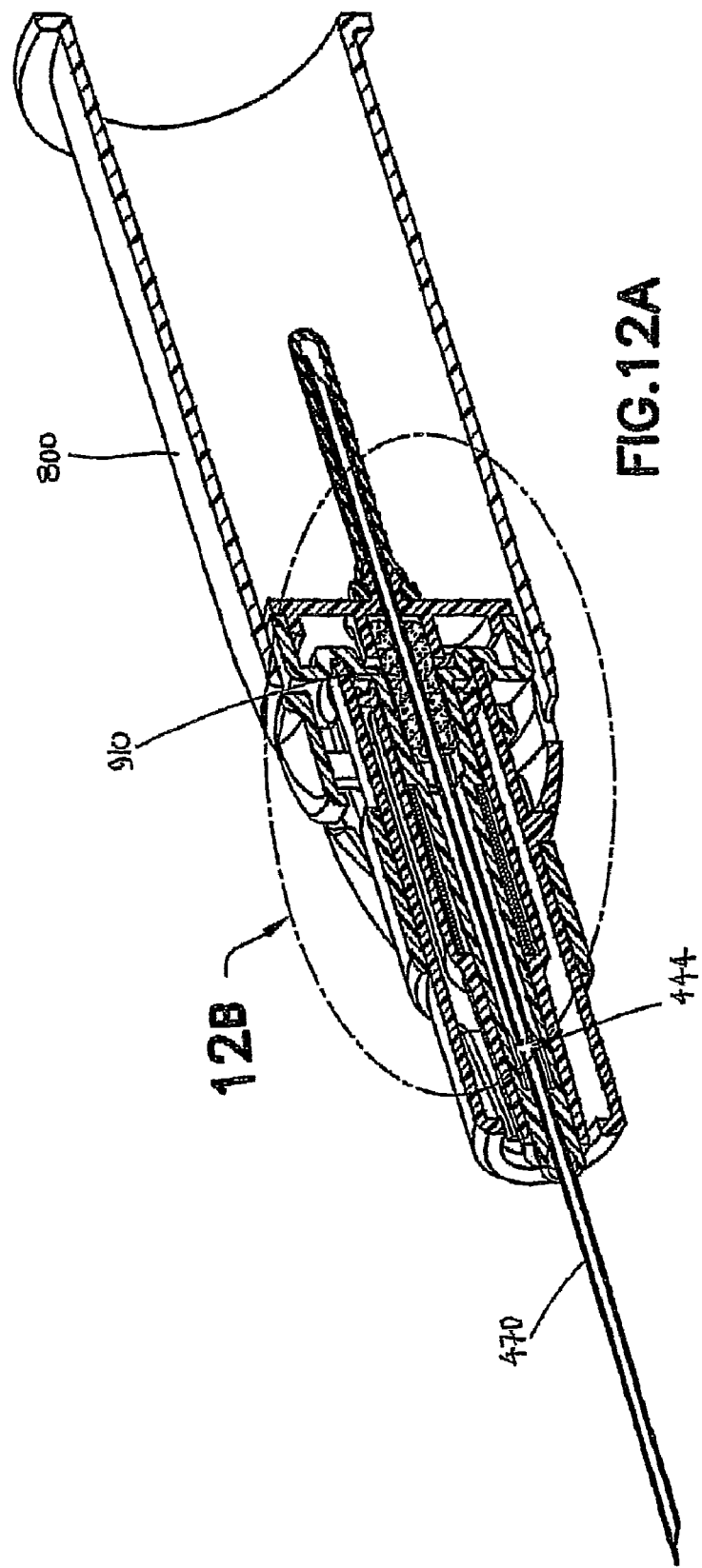

FLASHBACK BLOOD COLLECTION NEEDLE

CROSS REFERENCE TO RELATED APPLICATIONS

This application is a divisional of U.S. patent application Ser. No. 12/044,354 entitled "Flashback Blood Collection Needle" filed Mar. 7, 2008, which is hereby incorporated by reference in its entirety.

BACKGROUND OF THE INVENTION

1. Field of the Invention

The present invention relates to a device for collecting blood samples by performing venipuncture on a patient. More particularly, the present invention relates to a needle assembly for multiple sample blood collection that allows a phlebotomist to determine whether vein entry has occurred when collecting a blood sample from a patient into an evacuated blood collection tube.

2. Description of Related Art

Venipuncture is the primary method used for acquiring blood samples for laboratory testing. In performing venipuncture procedures, a phlebotomist must follow several steps simultaneously. Such steps include assessing the patient's overall physical and psychological condition so as to properly select a venipuncture site and technique. The phlebotomist must also select the proper corresponding equipment, perform the technique so as to control bleeding, and properly collect and identify fluid specimens for testing. The phlebotomist must ascertain all of these coinciding factors, as such factors may adversely affect the distension of the vein and the length of the venipuncture procedure.

Various venipuncture devices have been developed to address the above-described problems. These devices include products intended to assist the phlebotomist in confirming that vein entry has been made see e.g. U.S. Pat. Nos. 5,222, 502 and 5,303,713. Such a device contains a needle assembly with a housing that defines a chamber therein. A single cannula pointed at both ends is affixed to the housing. The intravenous (IV) end of the cannula is adapted for penetration of a patient's vein. The non-patient end of the cannula has a sealable sleeve and is adapted for penetration of a penetrable stop positioned within an evacuated container.

Upon vein entry with the intravenous end of the cannula, blood will flow through the cannula, into the sealable sleeve and into the housing chamber, which is clear or translucent for visualization ("flashback"). Once air is vented from the flashback chamber, the blood therein is pressurized each time the sealable sleeve is pushed toward the housing chamber upon activation of an evacuated container.

Due to the length of time between vein entry and flashback, the phlebotomist may erroneously believe that satisfactory vein entry has not been achieved since there is no immediate indication of vein entry in the see-through chamber. The phlebotomist may therefore unnecessarily repeat the venipuncture procedure, requiring replacement of the evacuated container and/or the needle assembly itself. Such a repetitive process prolongs the physical and emotional discomfort endured by the patient. In such cases, a phlebotomist may use a blood collection set to provide some entry indication, and will then incur the cost of the blood collection set, as well as the cost of a discard tube.

It would therefore be desirable to provide an improved blood collection device that permits blood flow through a relatively short needle directly into a flashback chamber, thereby providing immediate indication of successful vein entry.

SUMMARY OF THE INVENTION

The invention provides a needle assembly for the extraction of at least one fluid sample into an evacuated container for laboratory testing. The needle assembly provides a clear or translucent housing with sufficient dead space for blood to flow into a flashback chamber for visualization by the user to confirm successful vein entry, with an internal vent mechanism.

In one embodiment, the invention relates to a needle assembly comprising a housing defining a housing interior, a cannula having a patient puncture tip extending from a first end of the housing, and a non-patient puncture tip extending from a second end of the housing. The non-patient puncture tip and the patient puncture tip are in fluid communication with each other through the cannula, such that the sole communication path between the housing interior and the external environment is via the patient puncture tip. A porous vent is positioned within the housing interior to separate the housing interior into a first chamber and a second chamber, with the cannula being in fluid communication with the first chamber. The porous vent includes pores for passage of blood therethrough from the first chamber to the second chamber. The first chamber and the second chamber are configured such that upon insertion of the patient needle tip into a patient, blood flows through the cannula and into the first chamber without sealing the porous vent. Upon application of an evacuated container to the non-patient puncture tip, blood is drawn from the first chamber and air is drawn from the second chamber, thereby establishing a negative pressure within the second chamber with respect to an external environment of the needle assembly. Blood can thereafter be drawn into the first chamber and through the porous vent, with a negative pressure maintained in the second chamber.

In one embodiment, the cannula includes a first end comprising the patient puncture tip and a second end comprising the non-patient puncture tip, with an opening between the first end and the second end providing fluid communication between the cannula and the first chamber of the housing. In an alternate embodiment, the cannula comprises a first cannula having a patient puncture tip, with the needle assembly further comprising a second cannula including the non-patient puncture tip, with the first cannula and the second cannula substantially axially aligned and separated by a gap in fluid communication with the first chamber of the housing. A sleeve may also extend about the non-patient puncture tip.

In a particular embodiment, the first end of the housing comprises an elongate longitudinal first portion having a first diameter and the second end of the housing comprises a second portion having a second diameter larger than the first diameter of the first portion. In such an embodiment, the porous vent may be positioned within the housing interior between the first portion having a first diameter and the second portion having a second diameter. Alternatively, the porous vent may be positioned within the housing interior at a location spanning the transition between the first diameter of the first position and the second diameter of the second position.

In yet a further embodiment, a method of preventing leakage of blood from a needle assembly is provided. The method involves receiving blood through a patient puncture tip and into a first chamber of a needle assembly, with the needle assembly including a needle housing defining a housing interior; a cannula having the patient puncture tip extending from a first end of the needle housing; a non-patient puncture tip extending from a second end of the needle housing, the non-patient puncture tip and the patient puncture tip being in fluid communication with each other through the cannula; and a porous vent positioned within the housing interior and separating the housing interior into a first chamber and a second chamber. The cannula is in fluid communication with the first chamber such that the sole communication path between the housing interior and the external environment is via the patient puncture tip, and the porous vent includes pores for passage of blood therethrough from the first chamber into the second chamber. Fluid communication is established between the non-patient puncture tip and an evacuated collection container, such that blood contained within the first chamber is drawn into the evacuated collection container and air is drawn out of the second chamber through the porous vent. As such, a negative pressure is established within the second chamber relative to the external environment of the needle assembly, such that blood flows through the cannula into the first chamber and contacts the porous vent. Blood is then drawn through the pores of the porous vent toward the second chamber such that after removing the patient puncture tip from the vasculature of the patient any blood contained within the cannula is displaced away from the patient puncture tip based upon the negative pressure established within the second chamber.

Additionally, a further step may include establishing fluid communication between the non-patient puncture tip and a second evacuated collection container prior to drawing blood through the patient puncture tip and through the cannula into the second evacuated collection container, followed by releasing the fluid communication between the non-patient puncture tip and the second evacuated collection container.

In yet a further embodiment, the invention is directed to a method of collecting a sample of blood from a patient into an evacuated blood collection tube using a blood collection assembly having a patient needle tip and a non-patient needle tip and a housing having a flashback visualization chamber. The method involves using a needle assembly comprising a housing having a porous vent positioned therein to separate an interior of the housing into a first chamber forming the flashback visualization chamber and a second chamber, the first chamber and second chamber being configured such that air is drawn out of the second chamber through the porous vent and into the evacuated blood collection tube along with the blood sample, thereby establishing a negative pressure within the second chamber. The negative pressure causes blood to be drawn into the first chamber and contact the porous vent, such that after the patient needle tip is removed from the patient, the negative pressure within the second chamber draws blood from the patient needle tip toward the second chamber, thereby preventing leakage of blood from the patient needle tip.

DESCRIPTION OF THE DRAWINGS

FIG. 11A is a cross-sectional view of the needle assembly having a flash chamber of FIG. 8.
FIG. 11B is an enlarged cross-sectional view of a portion of the needle assembly of FIG. 11A.
FIG. 12A is a cross-sectional view of a needle assembly having a flash chamber used in connection with a blood collection assembly in yet a further embodiment.

DETAILED DESCRIPTION

The invention provides a needle assembly for blood collection that provides a visual indication of vein entry ("flashback") upon collection of a blood or other fluid sample from a patient into one or more evacuated blood collection tubes and inhibits leakage of the blood or fluid sample from the IV cannula on removal from the patient.

Figure 1:
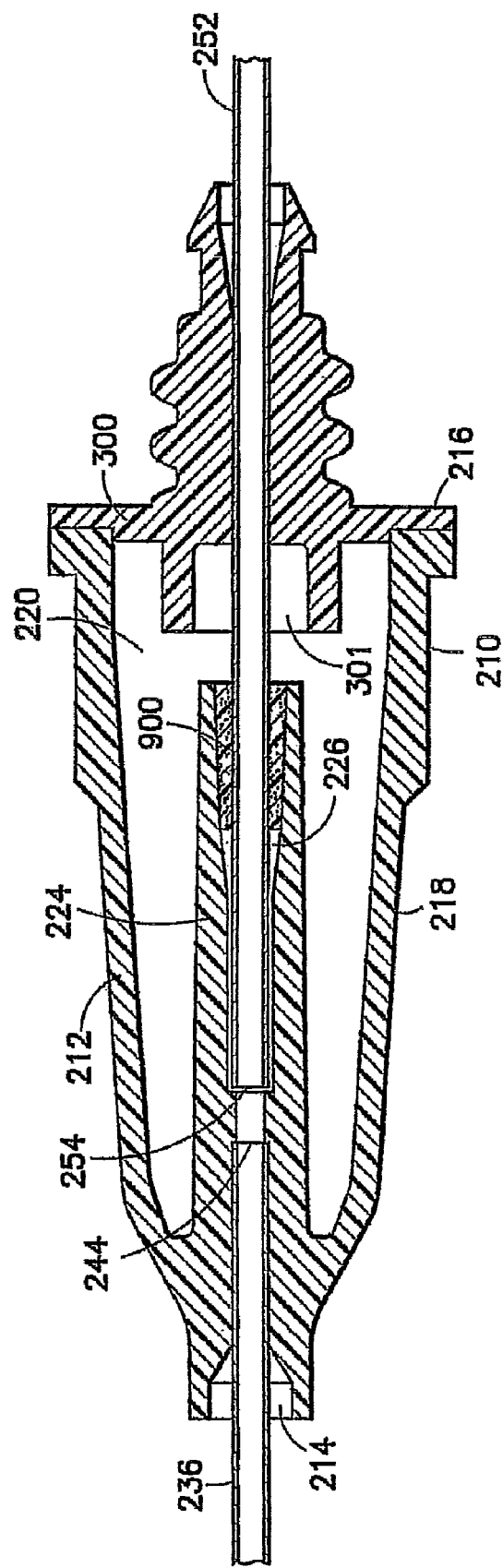
FIG. 1 is a cross-sectional view of a typical embodiment of the needle assembly of the present invention.

Various embodiments of the present invention are shown in FIGS. 1-7. With reference to FIG. 1, this embodiment is directed to a needle assembly 210 with a housing 212 having a fluid inlet end 214, a fluid outlet end 216 and a frustum-shaped exterior wall 218 extending between the ends. Exterior wall 218 defines the housing interior 220. Housing 212 further includes a cylindrical interior wall 224 that extends in the housing interior 220 from fluid inlet end 214 substantially concentrically with cylindrical exterior wall 218 to a vent plug 900. Cylindrical interior wall 224 and vent plug 900 define a flashback chamber 226.

Needle assembly 210 also includes a fluid inlet cannula 236 having an exterior end that defines a sharpened bevel and an interior end 244 that is mounted fixedly in fluid inlet end 214 of housing 212. Fluid inlet cannula 236 is characterized further by a substantially cylindrical lumen extending between the ends and communicating with the interior of housing 212.

Needle assembly 210 further includes a fluid outlet cannula 252. Outlet cannula 252 concludes a blunt interior end 254, an exterior end defining a sharpened bevel and a substantially cylindrical lumen extending between the ends. Portions of outlet cannula 252 between the ends are securely affixed in outlet end 216 of housing 212. Outlet cannula 252 is mounted so that interior end 254 passes substantially coaxially into interior wall 224 and so that interior end 254 of outlet cannula 252 substantially aligns axially with interior end 244 of inlet cannula 236. Additionally, interior end 254 of outlet cannula 252 is spaced only a small distance from interior end 244 of inlet cannula 236. An axial gap between interior end 254 of outlet cannula 252 and interior end 244 of inlet cannula 236 that is less than 0.5 mm may result in a flashback that is inconsistent.

Cylindrical interior wall 224 is dimensioned relative to outlet cannula 252 to achieve both desirable flow of blood through assembly 210 and to achieve effective flashback indication. In particular, cylindrical interior wall 224 preferably is dimensioned to provide a radial gap around outlet cannula 252 of about 0.2 mm, as indicated by dimension "c" in FIG. 1. This gap achieves a substantially laminar blood flow within flashback chamber 226 and prevents blood hemolysis. Additionally, the small radial gap between cylindrical inner wall 224 and outlet cannula 252 enables a drop of blood to be spread thinly across the radial gap in flashback chamber 226 to provide a magnified flashback indication with a very small volume of blood. Thus, an easily visualized flashback indication is achieved quickly at the first appearance of blood from interior end 244 of inlet cannula 236.

Needle assembly 210 further includes a sealable sleeve 261 mounted to fluid outlet end 216 of housing 212 and covering exterior end 258 of outlet cannula 252 when sealable sleeve 261 is in an unbiased condition. However, sealable sleeve 261 can be collapsed in response to pressure exerted by the stopper of an evacuated tube for urging exterior end 260 of outlet cannula 252 through both sealable sleeve 261 and stopper of an evacuated tube, as known in the art.

The above embodiment is described in terms of a vent plug. However, any vent mechanism is suitable. The vent mechanism may be, for example, a porous vent plug formed from a matrix or carrier material, typically hydrophobic, that is coated with, impregnated with, or otherwise, contains a hydrophilic material that swells on contact with aqueous or water containing substances. The hydrophobic carrier material can be but is not limited too, high-density polyethylene, polytetrafluoroethylene, ultra-high molecular weight polyethylene, Nylon 6, polypropylene, polyvinylidine fluoride and polyethersulfone. The swellable nature of the hydrophilic material thereby provides the sealing function in the vent upon contact with blood. It is also possible to use a porous vent plug that becomes sealed upon contact with blood using biological phenomena, e.g., by clotting and/or cell agglutination that blocks the vent; a superabsorbant material to seal the vent by swelling on contact with an aqueous fluid; or a one-way valve, (e.g., a thin flap such as plastic film covering a vent, a deformable seal such as a rubber or plastic duckbill valve, or a deformable wrap over a vent). It should be noted that any combination of these various mechanisms is also possible.

Figure 2:
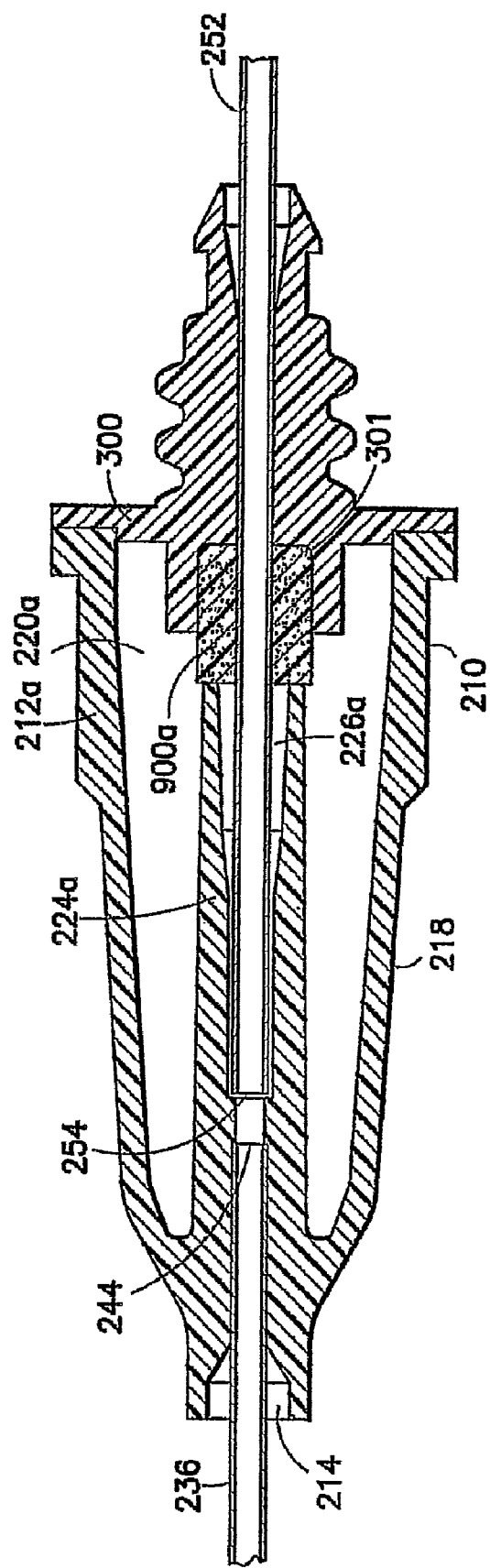
FIG. 2 is a cross-sectional view of a second embodiment.
Figure 3:
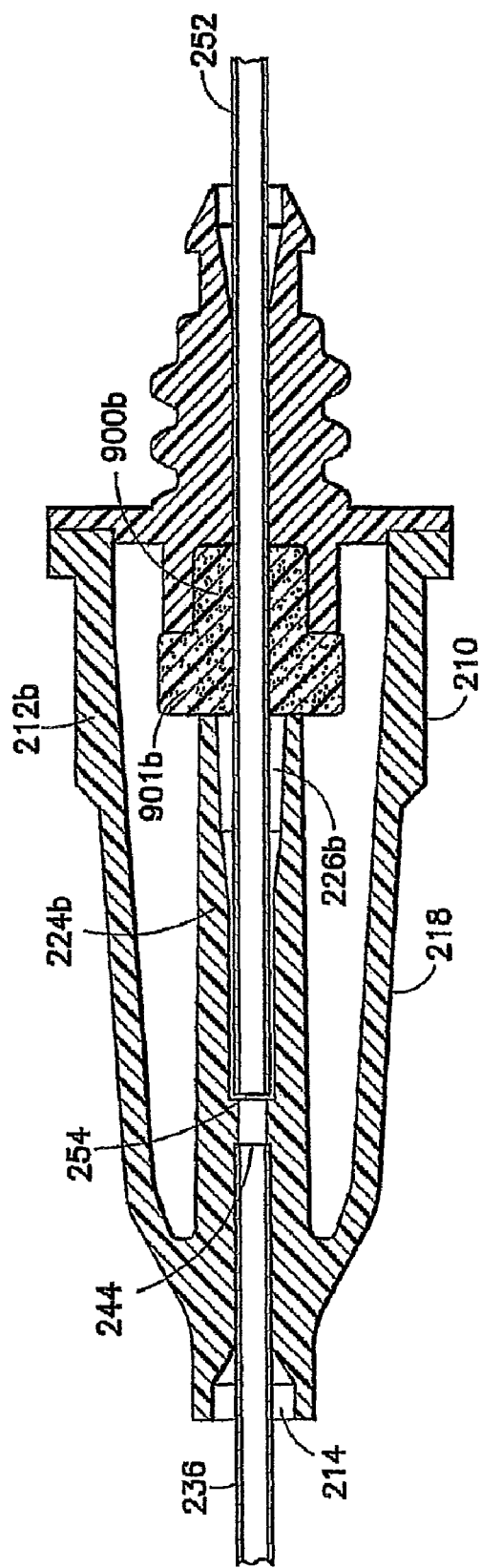
FIG. 3 is a cross-sectional view of a third embodiment.
Figure 4:
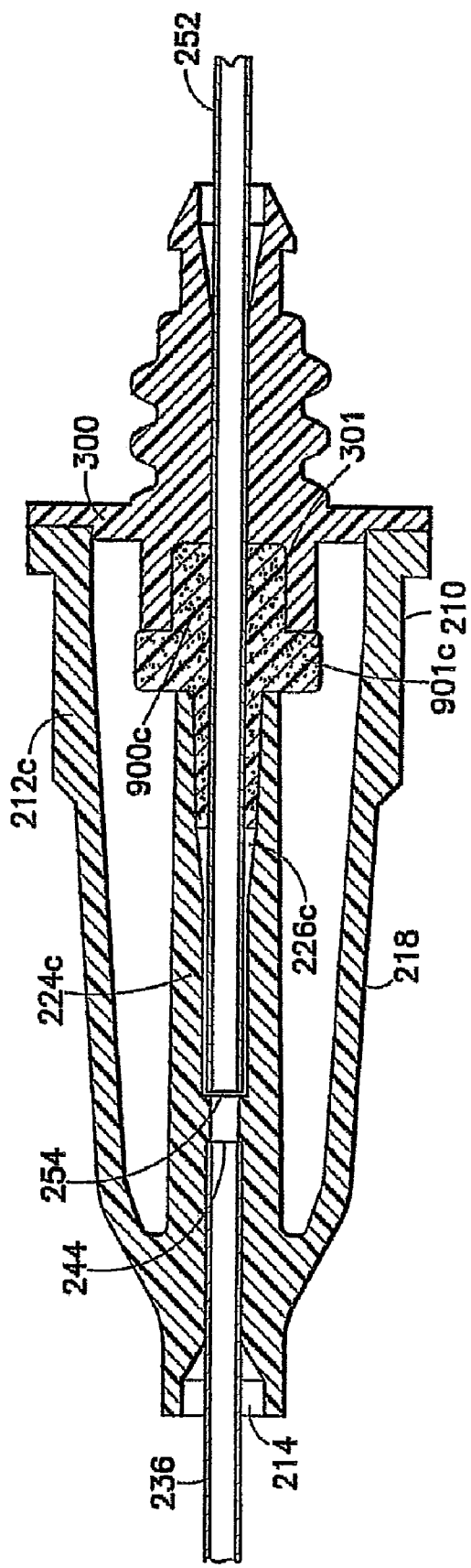
FIG. 4 is a cross-sectional view of a fourth embodiment.

FIGS. 2-4 show embodiments with varying vent plugs. FIG. 2 shows a vent plug 900a, which is located at the end of the cylindrical inner wall 224a and fitted into a recess 301 in the housing interior non-patient wall 300. FIG. 3 shows a vent plug in a similar location to that of FIG. 2, however, vent plug 900b has a shoulder 901b. FIG. 4 shows a vent plug 900c that is located both within the cylindrical inner wall 224c and the recess 301 in the housing interior non-patient wall 300, and has a shoulder 901c. The vent plug location in each of these embodiments is such that no air can flow out of the flashback chamber 226 into the housing interior 220 without passing through the vent mechanism (900a, b, c).

Figure 5:
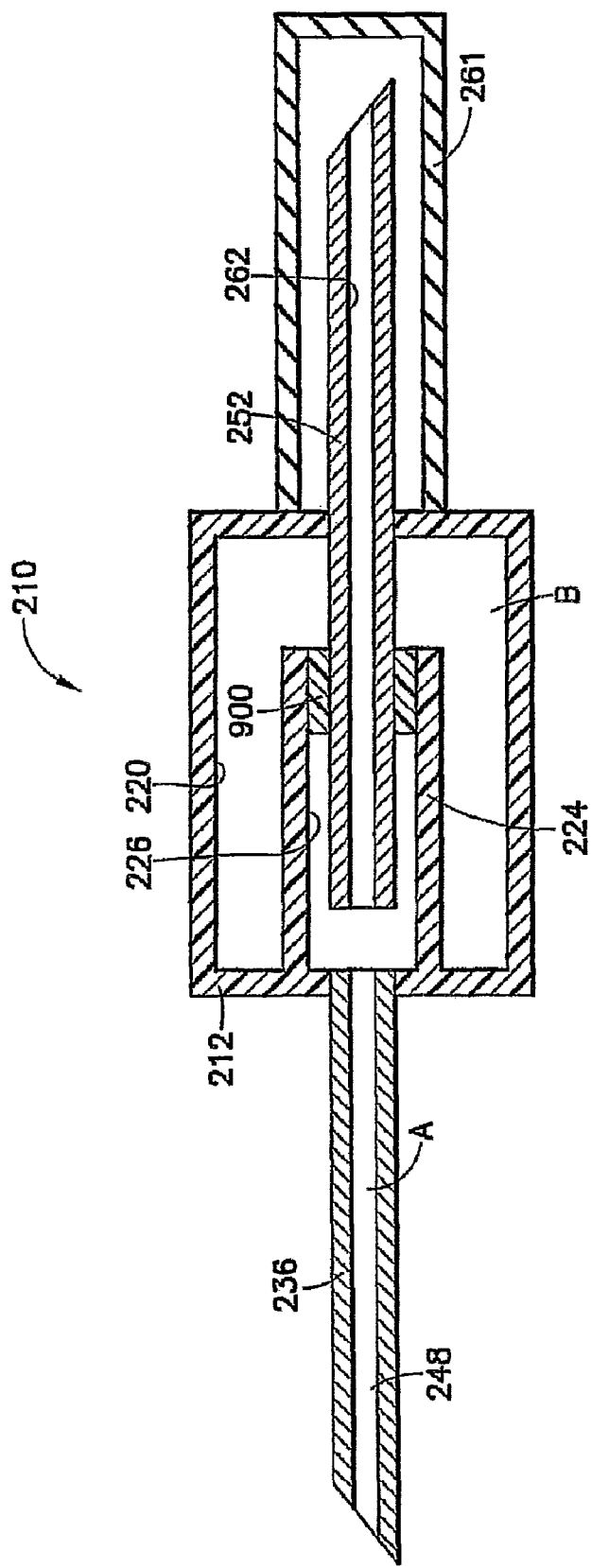
FIG. 5 is a schematic view of the needle assembly of FIG. 1 prior to use.
Figure 6:
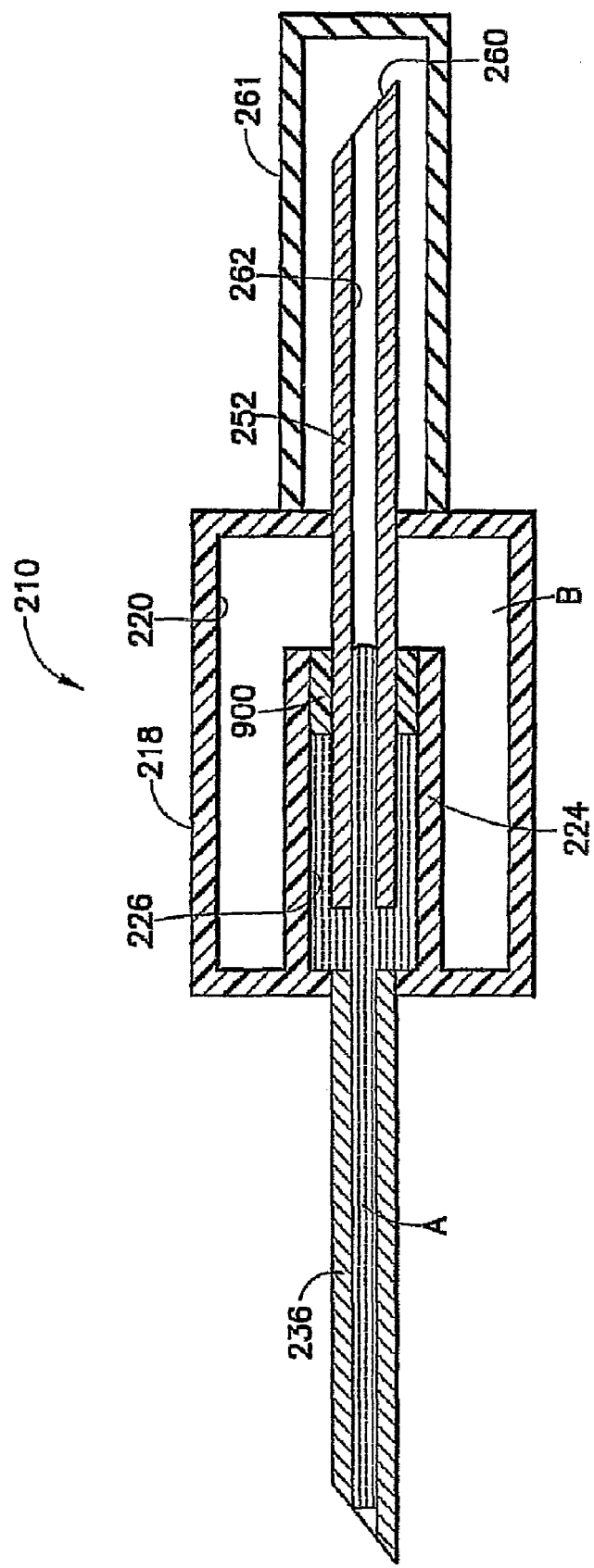
FIG. 6 is a schematic view similar to FIG. 5, but showing the first sign of venous entry.

FIGS. 5 and 6 provide schematic representations of the needle assembly 210 of FIG. 1 before and after a conventional venipuncture, in which, the needle assembly 210 is connected to a holder (not shown) and punctures the patient's skin to make a vein entry. Upon vein entry, blood enters the IV cannula 236 and flows toward the flashback chamber 226. The blood flows from inlet cannula 236 into the space between inlet and outlet cannula, such that blood flows both into the outlet cannula 252 and into flashback chamber 226. At this point in time, flashback chamber 226 indicates successful vein entry and reduces the volume of air present in housing 212 shown in FIG. 6. Air that was at atmospheric pressure within the lumen of the IV cannula 248, flashback chamber 226, housing interior 220, and the lumen of the non-patient cannula 262 prior to vein entry, thus experiences compression due to the influence of venous pressure and this air is therefore forced through the IV cannula 236 shown in FIG. 6 into the flashback chamber 226 and through the vent plug into chamber 220. Blood flow into housing interior 220 is prevented by the vent plug 900, which allows the pressurized air to flow through it, but seals on contact with blood, thereby trapping the compressed air (at venous pressure) in housing interior 220. Blood flow in the entire needle assembly ceases once the pressure within chamber 226 and the venous pressure are equal.

Once the steps set forth in the previous paragraph occur, and venous entry is visually confirmed by the phlebotomist, an evacuated container (not shown), is then inserted into the holder such that exterior end 260 of second cannula 252 penetrates the stopper of the container, as known in the art. Upon penetration of the stopper by second cannula 252, a negative pressure gradient is transmitted to chamber 226, causing blood to flow from chamber 226 into the container.

The needle assemblies described above desirably should be small for convenient use, but should be constructed to ensure reliable and rapid flashback. The occurrence of flashback in the needle assemblies described and illustrated above operate pursuant to the ideal gas law. In particular, at very low densities all gases and vapors approach ideal gas behavior and closely follow the Boyle's and Charles' laws given by:

$$P_1 V_1 = P_2 V_2$$

where:
 $P_1$ denotes the pressure of air within the needle assembly before needle insertion;
 $P_2$ denotes the pressure of air within the needle assembly after vein entry;
 $V_1$ denotes the volume of air within the needle assembly before vein entry; and
 $V_2$ denotes the volume of air within the needle assembly after vein entry.

Design parameters should keep the needle device as small as possible for easy use, while ensuring an appropriate volume as specified by the preceding equation. FIGS. 5 and 6 provide schematic representations of the needle assembly 210 of FIG. 1 for purposes of depicting the application of the ideal gas law. In this regard, A identifies the volume of lumen 248 through inlet cannula 236. B denotes the total volume of the housing interior 220, flashback chamber 226, lumen 242 through outlet cannula 252 and sealable sleeve 261. Referring again to the preceding equation, $P_1$ is the pressure within needle assembly 210 before use, and hence substantially equals atmospheric pressure. Atmospheric pressure will vary slightly from time to time and from location to location. However, for purposes of this analysis, atmospheric pressure $P_1$ will be assumed to be 760 mm Hg. $P_2$ in the preceding equation is the volume of the dead space in needle assembly 210 after vein entry. More particularly, after vein entry, blood will fill lumen 248 of inlet cannula 236, thereby reducing the volume to be occupied by gas in remaining portions of needle assembly 210 and hence increasing the pressure of air in the remaining portion of needle assembly 210. A needle assembly with dimensions approximately as shown in FIG. 1 will have a pressure $P_2$ of about 790 mm Hg at venous pressure (with tourniquet). $V_1$ in the preceding equation defines the volume of the total dead spaced in needle assembly 210 before use, and hence will equal A+B as shown in FIG. 5. $V_2$ defines the dead space in the device after vein entry, and with lumen 248 of inlet cannula 236 filled with blood. Hence, $V_2$ in the preceding equation will equal B. These input parameters can be employed to define a minimum desired size for the respective components of needle assembly 200 as shown in the following application of the ideal gas law equation.

$$P_1 V_1 = P_2 V_2$$

$$P_1 / P_2 = V_2 / V_1$$

$$760/790 = B/(A+B)$$

$$0.962 = B/(A+B)$$

$$0.962(A+B) = B$$

$$0.038B = 0.962A$$

$$B = 25.3A$$

Therefore, dead space in housing 212, outlet cannula 252 and sleeve 261 advantageously is at least 25.3 times the volume defined by lumen 248 through inlet cannula 236, and most advantageously is about 26 times the volume of lumen 248. However, other configurations are possible and will function as described herein.

The immediate response when an evacuated tube is placed in communication with outlet cannula 252 is to draw blood from the vein into tube (not shown). The highest-pressure gradient is always maintained between the vein and the evacuated tube. An axially aligned inlet cannula 236 and outlet cannula 252, therefore provide an unobstructed path for blood flow from the vein into evacuated tube.

When the requisite tubes are filled with blood, the needle assembly is removed from the vein. The sealed nature of the vent plug 900 inhibits the pressurized air within housing interior 220 from then moving into the flashback chamber 226 and into the inlet cannula 236, which could promote dripping of blood from the IV cannula tip.

Figure 7:
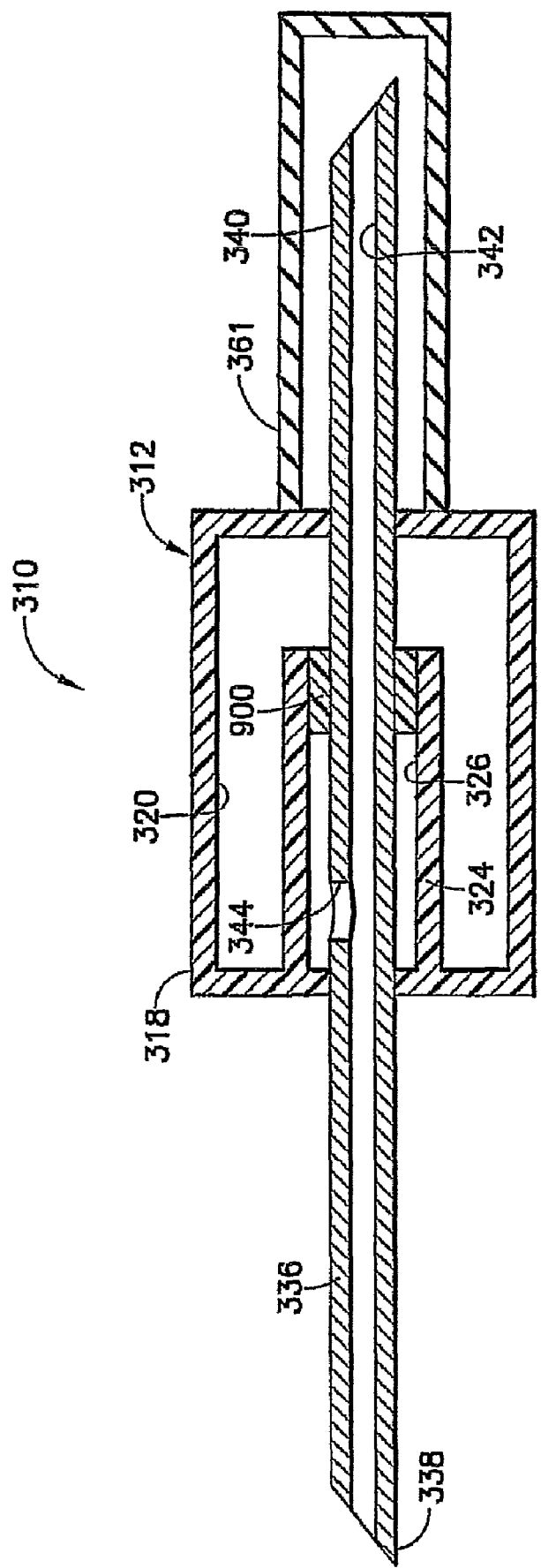
FIG. 7 is a schematic view of a fifth embodiment.
Figure 8:
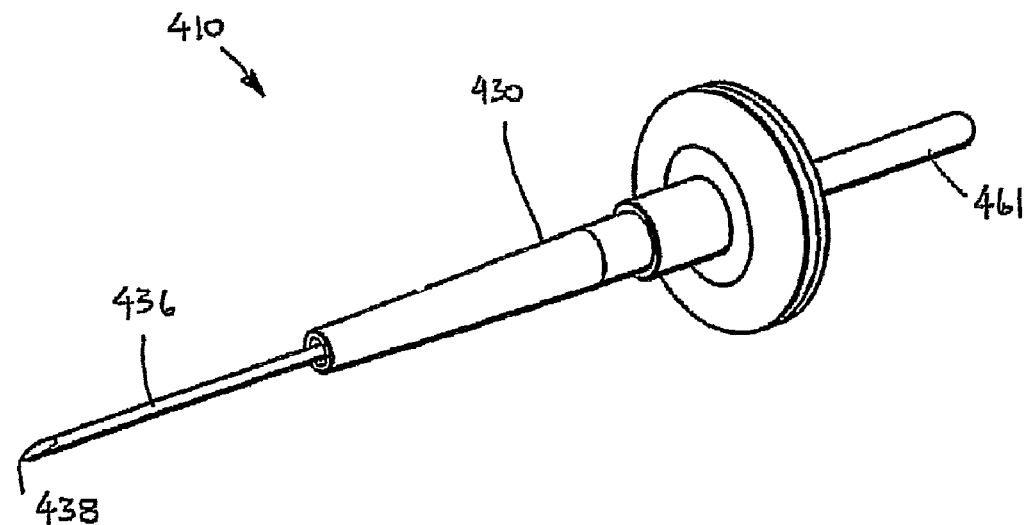
FIG. 8 is a perspective view of a needle assembly having a flash chamber in a further embodiment.
Figure 9:
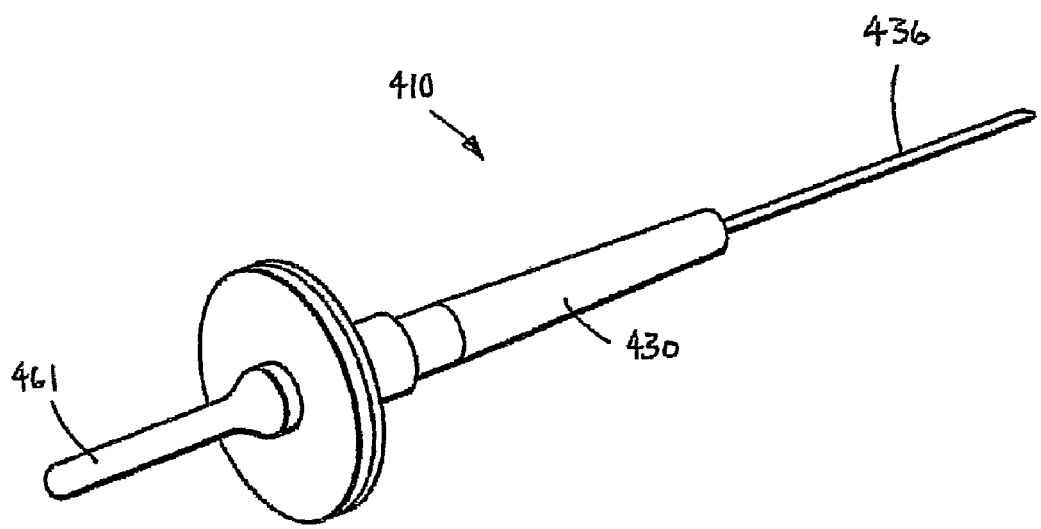
FIG. 9 is a rear perspective view of the needle assembly having a flash chamber of FIG. 8.

The preceding embodiments show structurally separate inlet and outlet cannulas that are axially aligned with one other and placed in close end-to-end relationship with one another. However, the principals of the invention described above also can be achieved with a single cannula formed with a transverse slot or aperture within the flashback chamber. For example, FIG. 7 schematically shows a needle assembly 310 with a housing 312 that is substantially identical to housing 212 described and illustrated above. Needle assembly 310 differs from needle assembly 210 in that a single double end needle cannula 336 is provided and passes entirely through housing 312. More particularly, needle cannula 336 includes a venous entry end 338, a non-patient end 340 and a lumen 342 extending therebetween. Portions of cannula 336 within inner wall 324 include a slot or aperture 344 to provide communication between lumen 342 and flashback chamber 336 within inner wall 324. Needle assembly 310 functions substantially in the same manner as needle assembly 210 described and illustrated above.

FIGS. 8-11 depict a needle assembly in yet a further embodiment of the invention. In certain embodiments of the needle assembly described with respect to FIGS. 1-7, the housing interior includes a vent plug 900, which seals the flashback chamber 226/326 from the housing interior 220/320. In such previously described embodiments, the vent plug is described as sealing upon flow of blood into the flashback chamber, thereby inhibiting any pressurized air that may build up within the housing chamber 220/320 (such as upon displacement of air from the flashback chamber 226/326 into the housing chamber 220/320 during the initial flash procedure) from moving in a reverse direction toward the inlet cannula. In the embodiment of FIGS. 8-11, a porous vent is positioned within the housing at a location such that the vent divides the housing into two chambers having sizes and dimensions to establish predetermined volumes thereto. Moreover, the porous vent remains porous to blood and does not seal upon contact with blood. Desirably the blood does not contact the porous vent at the initial flash indication, but such contact occurs at a later point during use of the assembly, as will be described in more detail herein.

For example, FIGS. 8-11 show a needle assembly 410 similar to that described in connection with FIG. 1-6 above. As shown in FIGS. 8-11, needle assembly 410 includes a housing 412 having a fluid inlet end or first end 414 and a fluid outlet end or second end 416. Needle assembly 410 includes exterior wall 418 defining the housing interior. Exterior wall 418 extends generally longitudinally at the first end 414 forming an elongate longitudinal first portion 419 having a first diameter. At second end 416, exterior wall 418 forms a second portion 421 that has a second diameter that is generally larger than the first diameter of the first portion 419. Accordingly, housing 412 may form a structure having a generally T-shaped cross-section. The exterior wall 418 at second end 416 may be a separate element 428 that is attachable to main body portion 430 forming housing 412, thereby assisting in manufacture and assembly of needle assembly 410. First portion 419 and second portion 421 may be arranged relative to each other in a variety of arrangements, so long as they are capable of functioning for transport of air therebetween as discussed herein.

Needle assembly 410 further includes a fluid inlet cannula 436 extending from first end 414 of housing 412. Fluid inlet cannula 436 includes an exterior end 439 that defines a sharpened bevel at patient puncture tip 438, and extends within first end 414 of housing 412, and may be fixedly mounted therein. Fluid inlet cannula 436 is characterized further by a substantially cylindrical lumen extending between the ends and communicating with the interior of housing 412.

Figure 10:
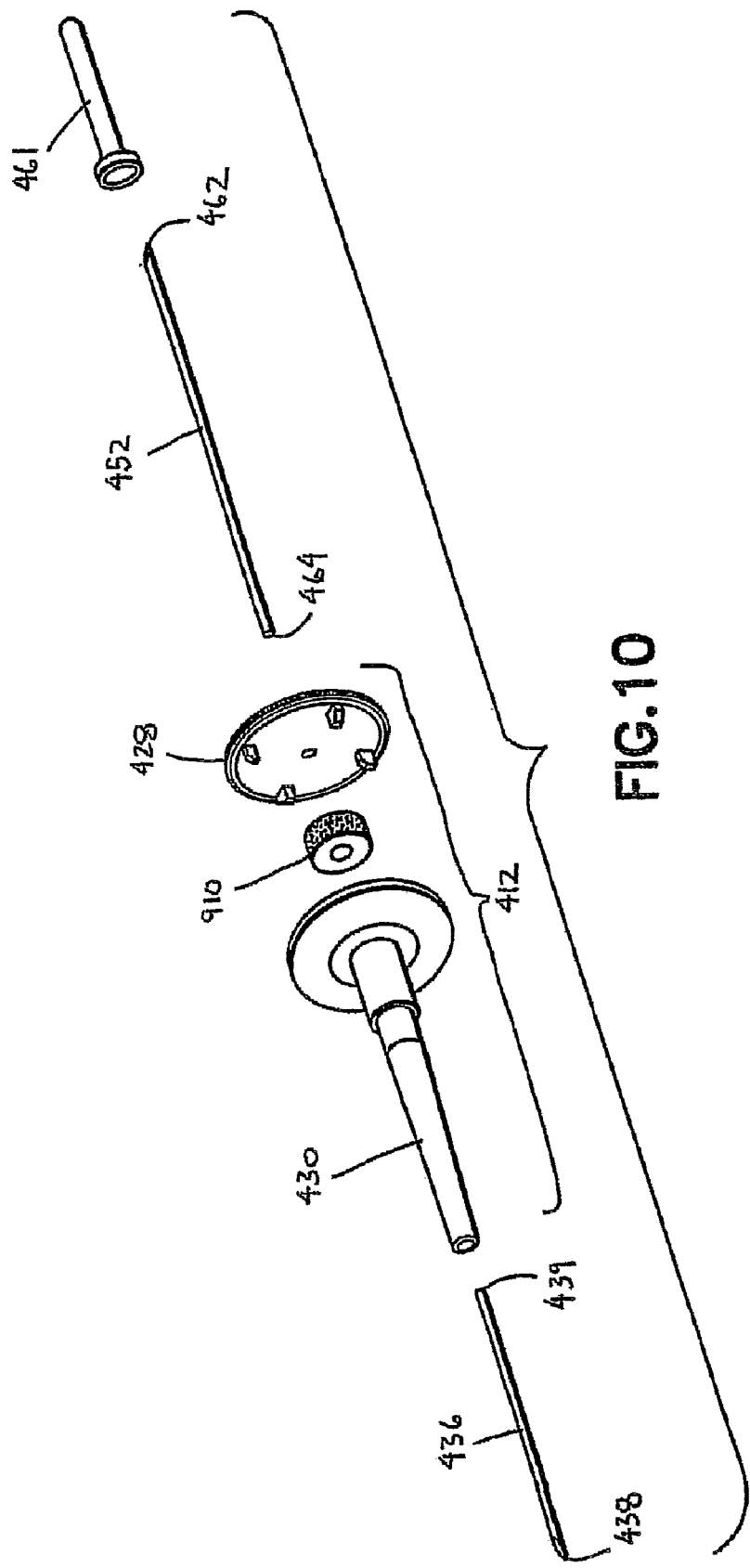
FIG. 10 is an exploded view of the needle assembly having a flash chamber of FIG. 8.

Needle assembly 410 also includes a non-patient puncture tip extending from second end 414 of housing 412. As seen in FIG. 10, this may be accomplished by providing needle assembly 410 with a second cannula in the form of fluid outlet cannula 452. In particular, the end of fluid outlet cannula 452 may define a sharpened bevel forming non-patient puncture tip 462. Fluid outlet cannula 452 extends within second end 416 of housing 412, and may be fixedly mounted therein. Fluid outlet cannula 452 is characterized further by a substantially cylindrical lumen communicating with the interior of housing 412. Outlet cannula 452 is mounted within housing 412 so that an interior end 464 passes substantially coaxially therein such that outlet cannula 452 substantially aligns axially with the interior end of inlet cannula 436. Desirably, this is achieved by mounting outlet cannula 452 at a location adjacent second end 416 of housing 412, such that the interior end 464 of outlet cannula 452 extends within housing 412 to a location adjacent the interior end 439 of inlet cannula 436. As seen in FIG. 11B, the interior end 464 of outlet cannula 452 is spaced only a small distance from the interior end 439 of inlet cannula 436, thereby forming an axial gap therebetween for flow of blood into flashback chamber 426 about outlet cannula 452. The distance between the interior end 464 of outlet cannula 452 and the interior end 439 of inlet cannula 436 forming the axial gap is sufficient to provide for flow of blood into flashback chamber 426 based upon the patient's blood pressure after venipuncture. In certain embodiments, an axial gap that is less than 0.5 mm may result in a flashback that is inconsistent.

As seen in FIG. 11B, fluid inlet cannula 436 and fluid outlet cannula 452 are positioned and dimensioned within housing 412 so as to achieve both desirable flow of blood through assembly 410 and to achieve effective flashback indication. In particular, wall 418 of housing 412 is dimensioned to provide a radial gap around outlet cannula 452 of about 0.2 mm at an area surrounding the internal end 464 thereof. This gap achieves a substantially laminar blood flow within flashback chamber 426 and prevents blood hemolysis. Additionally, the small radial gap between the inner surface of wall 418 and outlet cannula 452 at the area surrounding the internal end 464 enables a drop of blood to be spread thinly across the radial gap in flashback chamber 426 to provide a magnified flashback indication with a very small volume of blood. Thus, an easily visualized flashback indication is achieved quickly at the first appearance of blood within flashback chamber 426. It is contemplated that internal end 464 of outlet cannula 452 may be partially supported within housing 412, so long as blood flow into flashback chamber 426 is achieved about the internal end 464.

Figure 12B:
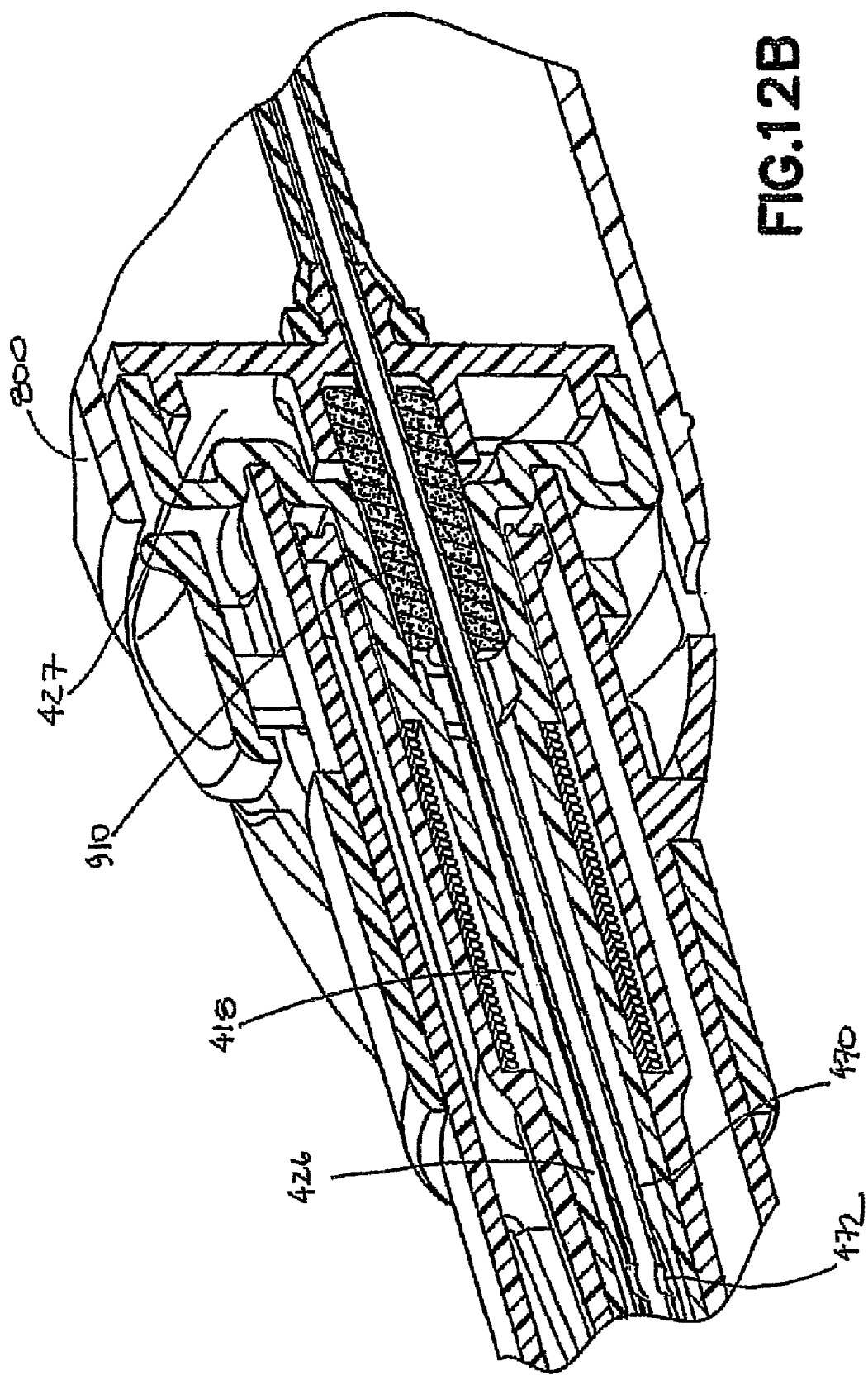
FIG. 12B is an enlarged sectional view of a portion of the needle assembly of FIG. 12A.

In an alternate arrangement, a single cannula is provided, similar to that embodiment discussed in connection with FIG. 7. Such an arrangement is depicted in the embodiment of FIGS. 12A and 12B (shown in connection with a blood collection assembly as will be described in more detail herein). In such an arrangement, the fluid inlet cannula and the fluid outlet cannula represent one single cannula 470, having a patient puncture tip 438 a non-patient puncture tip 462, and a lumen 442 extending therethrough, and with the body of the cannula 470 being fixedly attached to a portion of the housing 412 and passing entirely through housing 412. A portion of cannula 470 extending through housing 412 includes one or more openings such as a slot or aperture 444 to provide communication between lumen 442 and flashback chamber 436 within housing 412. In the embodiment seen in FIGS. 12A and 12B, two separate apertures are shown on opposing sides of cannula 470, although it is contemplated that any number of such openings can be included to provide for blood flow into flashback chamber 436.

Returning to the embodiment of FIGS. 8-11, needle assembly 410 further includes a sealable sleeve 461 mounted to fluid outlet end 416 of housing 412. This may be accomplished by providing a mounting protrusion 429 at second end 416 of housing 412, such as on element 428, with sealable sleeve 461 representing an elastomeric element that can be frictionally fit or otherwise affixed over protrusion 429. Sealable sleeve 461 covers non-patient puncture tip 462 at the exterior end of outlet cannula 452 when sealable sleeve 461 is in an unbiased condition. However, sealable sleeve 461 can be collapsed in response to pressure exerted by the stopper of an evacuated tube for urging exterior end 460 of outlet cannula 452 through both sealable sleeve 461 and the stopper of an evacuated tube, as known in the art.

The embodiment of FIGS. 8-11 further includes a porous vent 910 positioned within the interior of housing 412. Porous vent 910 is positioned within housing 412 to divide housing 412 into two distinct chambers, namely, a first chamber represented by flashback chamber 426 and a second chamber represented by secondary chamber 427. Porous vent 910 may be constructed of a suitable material as described above with respect to vent plug 900, albeit without the hydrophilic material that swells on contact. In this manner, porous vent 910 is adapted to vent air therethough, and represents a porous structure including a plurality of pores that allow for passage of blood therethrough. As discussed in more detail herein, during use of needle assembly 410, the internal pores within porous vent 910 at least partially fill with blood due to the negative pressure established within secondary chamber 427. Such filled pores in combination with the negative pressure within secondary chamber 427 prevent air flow between the secondary chamber 427 and the flashback chamber 426, and provide for fluid resistance of the blood flow through porous vent 910, as will be described in further detail.

Desirably, porous vent 910 is positioned within the interior of housing 412 between first portion 419 and second portion 421. In this manner, first portion 419 of housing 412 essentially defines the flashback chamber 426, and second portion 421 of housing 412 essentially defines the secondary chamber 427. Alternatively, porous vent 910 may be positioned within the interior of housing 412 at a location spanning the transition between the first diameter of first portion 419 and the second diameter of second portion 421, as shown in the embodiment of FIGS. 12A and 12B. In any event, porous vent 910 is generally a cylindrically-shaped member with a central opening therein axially encircling a portion of the cannula, particularly fluid outlet cannula 452.

The interior volume of housing 412 is defined by the sum of the volumes of flashback chamber 426 and secondary chamber 427 as well as the volume represented by the pores of porous vent 910. Such interior volume is configured so as to provide for certain attributes to the needle assembly 410, in particular with respect to the ability of the secondary chamber 427 to be at least partially evacuated of a portion of the air therein to establish a negative pressure therein upon application of an evacuated tube to needle assembly 410 during use thereof. Such negative pressure within secondary chamber 427 draws blood through the pores of porous vent 910 based on when blood contacts porous vent 910 and partially fills the pores thereof. In a particular embodiment of the invention, the overall interior volume of housing 412 may be from about 300 mm$^3$ to about 400 mm$^3$. Such a volume is particularly useful for the intended use of needle assembly 410 for conventional venipuncture for drawing a blood sample from a patient using a needle cannula having a conventional gauge for venipuncture as is known in the art. With such an internal volume, porous vent 910 is desirably positioned within housing interior so as to define flashback chamber 426 as having a volume that represents from about 5 percent to about 20 percent of the total overall volume of housing 412, desirably from about 7 percent to about 12 percent of the total overall volume of housing 412, including the volume of secondary chamber 427 and the volume of the pores within porous vent 910. Such a ratio of the flashback chamber 426 to the total overall volume of the housing 412 assures that flashback chamber 426 has sufficient volume to properly visualize the initial flash, and desirably while preventing blood from fully contacting the porous vent 910 at initial venipuncture, based on the initial build-up of pressure within secondary chamber 427 caused by venous pressure forcing the blood into flashback chamber 426. Such volume ratios are effective for the intended use as described in further detail herein, wherein blood flowing into flashback chamber 426 upon initial venipuncture does not contact porous vent 910, and wherein at least a portion of the air is drawn out from secondary chamber 427 based upon application of an evacuated blood collection tube to the needle assembly 410. In this manner, secondary chamber 427 can effectively draw blood from within flashback chamber 426 and from within fluid inlet cannula 426 toward secondary chamber 427, such as into and through porous vent 910, when patient puncture tip 438 is removed from the patient and is exposed to the external environment. In one particular embodiment, the total interior volume of the housing 412 is about 380 mm$^3$, with the flashback chamber 426 having a volume of about 30 mm$^3$, the secondary chamber 427 having a volume of about 300 mm$^3$, and the pores of the porous vent 910 representing a volume of about 50 mm$^3$.

Needle assembly 410 may be assembled as follows. Fluid inlet cannula 436 is positioned through first end 414 of housing 412 such that the open interior end 439 is positioned within an interior portion of housing 412 at first portion 419 and patient puncture tip 438 extends externally of first end 414. Fluid outlet cannula 452 is positioned within housing 412 through the opposite end, such that open internal end 464 is positioned within an interior portion of housing 412 at first portion 419 adjacent interior end 439 of fluid inlet cannula 436, with a slight gap therebetween, and with non-patient puncture tip extending externally of second end 416. Fluid inlet cannula 436 and fluid outlet cannula 452 may be affixed therein in any known manner, desirably through a medical grade adhesive.

In alternate embodiments including only a single cannula 470, such cannula 470 is affixed within housing 412 such that opening 472 is positioned within the interior of housing 412 at first portion 419, with patient puncture tip 438 extending externally of first end 414 and non-patient puncture tip 462 extending externally of second end 416.

Porous vent 910 is then inserted within housing 412 and positioned over fluid outlet cannula 454 (or over the single cannula 470), and element 428 is thereafter affixed to the second end 416, enclosing the interior of housing 412. Sealable sleeve 461 is then affixed over protrusion 429. As such, the interior of housing 412 is closed from the external environment, with the sole path for fluid communication between the interior of housing 412 and the external environment being provided through the patient puncture tip 438.

Needle assembly 410 assembled as such can be used in connection with a blood collection tube holder 800, as depicted in the embodiment shown in FIG. 12. Such assembly may be accomplished through the rear open end of blood collection tube holder 800, so that the entire needle assembly 410 is inserted to a portion where at least patient puncture tip 438 and at least a portion of inlet cannula 436 extend out through the front end of blood collection tube holder 800. In embodiments where second portion 421 of needle assembly 410 is radially larger than first portion 419, such an insertion and arrangement enables the secondary chamber 427 to be fully contained within the internal space within collection tube holder 800, and with flashback chamber 426 extending out from a front end thereof.

In use, needle assembly 410 may be provided with collection tube holder 800 attached thereto. Patient puncture tip 438 is inserted through the skin of a patient and into the patient's vasculature, desirably into a vein. Upon venipucture, a closed environment is achieved within housing 412, since housing 412 is an entirely closed structure, and since sealable sleeve 461 closes off the only outlet of housing 412 (i.e., fluid outlet cannula 452). The patient's blood pressure causes blood to flow through patient puncture tip 438, into fluid inlet cannula 436, and out interior end 439 (or through opening 472 in the embodiment of FIG. 12), into flashback chamber 426 surrounding interior end 464 of outlet cannula 452. The transparent or translucent nature of housing 412 permits visualization of the blood within flashback chamber 426, providing an indication that venipuncture is achieved.

Since the interior of housing 412 is a closed environment, the flow of blood into flashback chamber 426 causes air to be trapped within the housing interior, including within flashback chamber 426, porous vent 910 and secondary chamber 427, as well as within fluid outlet cannula 452, causing such trapped air to be slightly pressurized therein. Flashback chamber 426 and secondary chamber 427 are configured through their size and dimensions such that the volumes thereof permit blood to flow into flashback chamber 426 at this initial venipucture, but the build up of air pressure within the pores of porous vent 910 and within secondary chamber 427 prevents blood from fully contacting porous vent 910, and desirably prevents blood from even partially contacting porous vent 910 at the initial venipuncture.

After such initial venipuncture and flash visualization, a sample collection container having a negative pressure therein, such as an evacuated blood collection tube (not shown) as is commonly known in the art, is inserted within the tube holder 800. The stopper (not shown) of such evacuated container contacts and displaces sealable sleeve 461, causing non-patient puncture tip 462 to puncture through sealable sleeve 461 and through the stopper of the evacuated container. At this point, fluid communication is established between the non-patient puncture tip 462 and the interior of the evacuated collection container. The negative pressure within the evacuated collection container draws the blood that has collected within flashback chamber 426 into fluid outlet cannula 452 and into the evacuated collection container. Along with the blood within flashback chamber 426, the negative pressure within the evacuated collection container will also draw at least a portion of the air out of the flashback chamber 426 and out of the secondary chamber 427 through the pores of porous vent 910, toward and into the evacuated collection container. In addition, the close proximity and alignment of fluid outlet cannula 452 and fluid inlet cannula 426 causes blood to be drawn from fluid inlet cannula 436 and from the patient, simultaneously with such air being drawn from the flashback chamber 426 and secondary chamber 427.

Such drawing of air reduces the pressure within the flashback chamber 426 and the secondary chamber 427, establishing a negative pressure therein with respect to the patient's bloodstream and with respect to the external environment. This negative pressure that has been established within the interior of housing 412, and specifically within flashback chamber 426 and secondary chamber 427, draws additional blood from within fluid inlet cannula 436 and from the patient into flashback chamber 426, with the blood contacting porous vent 910. With such blood filling flashback chamber 426, the blood fully contacts the surface of porous vent 910 that extends within flashback chamber 426, and begins to fill the pores of porous vent 910. Such filling of the pores of porous vent 910 that are directly at the interface of porous vent 910 and flashback chamber 426 closes off the porous vent from airflow therethrough, but does not fully act as a seal, in that the blood does not cause the material of the porous vent to swell or close off to air flow, but instead merely physically fills the voids within the porous vent. Moreover, since a portion of the air within secondary chamber 427 has been drawn out from secondary chamber 427, secondary chamber 427 represents a closed chamber with a negative pressure therein relative to the external environment. Secondary chamber 427 will therefore continue to have a drawing effect on the blood within the pores of porous vent 910 and within flashback chamber 426 through the pores of porous vent 910 toward secondary chamber 427, without releasing any air from the secondary chamber 427 in the opposite direction due to the pores of porous vent 910 at the interface of the flashback chamber 426 being filled with blood, thereby effectively preventing air flow through porous vent 910 due to the filled pores. The draw created by the negative pressure within secondary chamber 427 has a fluid resistance based on the blood filling the pores of porous vent 910 and based on the tortuous path created by the pores of porous vent 910, and therefore is a gradual draw with reduced fluid movement.

At this point, the evacuated collection container and the secondary chamber 427 are both at a negative pressure with respect to the external environment (and with respect to the patient's bloodstream), and therefore both effect a draw from the fluid inlet cannula 436. This mutual drawing effect may essentially establish an equilibrium within the flashback chamber 426, such that the blood contained within the flashback chamber 426 is not drawn toward or into either the secondary chamber 427 through the pores of porous vent 910 or into the evacuated collection container through the fluid inlet cannula 436, but instead essentially remains within flashback chamber 426 in a steady state. The negative pressure of the evacuated collection container draws blood directly from the patient through fluid inlet cannula 436, due to the close proximity and alignment of fluid outlet cannula 452 and fluid inlet cannula 426, as well as due to the equilibrium established within flashback chamber 426 (based on the opposite draw forces between the evacuated collection container and the evacuated secondary chamber 427). The continual draw of blood into the evacuated collection container gradually causes the pressure within the collection container to increase.

Once the evacuated collection container is filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462. Absent such draw from the negative pressure of the evacuated collection tube, the negative pressure within the secondary chamber 427 effects a slight draw on the blood within flashback chamber 426 through the pores of porous vent 910. Such draw, however, is slow and gradual, due to the tortuous path of blood flow through the pores of porous vent 910.

Additional evacuated collection containers can thereafter be inserted into tube holder 800 and used for sample collection through non-patient puncture tip 462 as described above, by placing a second evacuated collection container within the holder 800 and establishing fluid communication between the non-patient puncture tip 462 and the interior of the evacuated collection container by puncturing the stopper, as discussed. In such further sampling, the evacuated collection container and the secondary chamber 427 are both at a negative pressure, and therefore both effect a draw from the fluid inlet cannula. As above, this effect essentially establishes an equilibrium within the flashback chamber 426, thereby preventing the blood contained within the flashback chamber 426 from being drawn toward or into either the secondary chamber 427 (through the porous vent 910). The negative pressure of the evacuated collection container draws blood directly from the patient through fluid inlet cannula 436 as discussed above, due to the close proximity and alignment of fluid outlet cannula 452 and fluid inlet cannula 426. Once any such additional evacuated collection containers are filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462.

Once all of the desired blood samples have been drawn in this manner, patient puncture tip 438 is removed from the vasculature of the patient (i.e. from the bloodstream), thereby exposing the opening of patient puncture tip 438 to the external environment. Since the sole communication path between the housing interior and the external environment is through patient puncture tip 438, the negative pressure established within secondary chamber 427 relative to the external environment will affect a gradual draw on the blood contained within flashback chamber 426 and within fluid inlet cannula 436 toward and through porous vent 910. Such drawing effect will displace and move any blood contained within fluid inlet cannula 436 away from patient puncture tip 438, toward secondary chamber 427, thereby preventing any blood from leaking from patient puncture tip 438 out of fluid inlet cannula 436. Such negative pressure within secondary chamber 427 may continue to have a gradual drawing effect through the porous vent 910 for a prolonged period of time after removal of patient puncture tip 438 from the patient, and may draw all of the remaining blood contained within fluid inlet cannula 436 and flashback chamber 426 through porous vent 910 and/or into secondary chamber 427. Needle assembly 410 can then be properly disposed of in known manner.

The relative dimensional calculations, volumes and pressures apply to both illustrated and unillustrated embodiments of the invention. Accordingly, the scope of the as defined by the appending claims is not limited to the specific illustrated embodiments. Various other changes and modifications may be effected therein by one skilled in the art without departing from the scope or spirit of the invention, and it is intended to claim all such changes and modifications as fall within the scope of the invention.

What is claimed is:

1. A needle assembly comprising:
a housing defining a housing interior, said housing comprising a patient puncture tip extending from a first end of the housing and a non-patient puncture tip extending from a second end of the housing, the non-patient puncture tip and the patient puncture tip being in fluid communication with each other within the housing interior,
a porous vent positioned within the housing interior separating the housing interior into a first chamber and a second chamber, the porous vent including pores for passage of blood therethrough from the first chamber to the second chamber, and
a sleeve extending about the non-patient puncture tip,
wherein the sole communication path between the housing interior and the external environment is via the patient puncture tip.

2. The needle assembly of claim 1, wherein the first chamber and the second chamber are configured such that upon insertion of the patient puncture tip into a patient blood flows into the first chamber without sealing the porous vent, and upon application of a negative pressure source to said non-patient puncture tip, blood is drawn from said first chamber and air is drawn from said second chamber, thereby establishing a negative pressure within said second chamber with respect to an external environment of the needle assembly.

3. The needle assembly of claim 1, further comprising a single cannula extending through the housing, said single cannula including and a lumen extending therethrough, a first end comprising the patient puncture tip, a second end comprising the non-patient puncture tip, and an opening through the cannula into the lumen at a location between the first end and the second end providing fluid communication between the lumen of the cannula and the first chamber of the housing.

4. The needle assembly of claim 1, further comprising a first cannula extending from the housing and comprising the patient puncture tip, and a second cannula extending from the housing and comprising the non-patient puncture tip, the first cannula and the second cannula being substantially axially aligned within said housing interior and separated from each other by a gap in fluid communication with the first chamber of the housing.

5. The needle assembly of claim 1, wherein upon at least a portion of air being drawn from said first chamber and said second chamber, said second chamber draws blood from the first chamber through the porous vent.

6. The needle assembly of claim 1, wherein at least a portion of said housing forming said first chamber is formed from a transparent or translucent material.

7. The needle assembly of claim 1 wherein said porous vent is formed from a porous hydrophobic carrier material.

8. The needle assembly of claim 1, wherein the first end of the housing comprises an elongate longitudinal first portion having a first diameter and the second end of the housing comprises a second portion having a second diameter larger than the first diameter of the first portion.

9. The needle assembly of claim 8, wherein the porous vent is positioned within the housing interior between the first portion having the first diameter and the second portion having the second diameter.

10. The needle assembly of claim 8, wherein the porous vent is positioned within the housing interior at a location spanning the transition between the first diameter of the first portion and the second diameter of the second portion.

11. A needle assembly comprising:
a housing defining a housing interior, said housing comprising a patient puncture tip extending from a first end of the housing and a non-patient puncture tip extending from a second end of the housing, the non-patient puncture tip and the patient puncture tip being in fluid communication with each other, wherein the sole communication path between the housing interior and the external environment is via the patient puncture tip; and
a porous vent positioned within the housing interior to separate the housing interior into a first chamber and a second chamber with the patient puncture tip and the non-patient puncture tip both in fluid communication with the first chamber of the housing, the porous vent including pores for passage of blood therethrough from the first chamber to the second chamber,
wherein the first chamber and the second chamber are configured such that upon insertion of the patient puncture tip into a patient blood flows into the first chamber without sealing the porous vent, and upon application of a source of negative pressure to said non-patient puncture tip, blood is drawn from said first chamber and air is drawn from said second chamber, thereby establishing a negative pressure within said second chamber with respect to an external environment of the needle assembly.

12. The needle assembly of claim 11, further comprising a single cannula extending through the housing, said single cannula including and a lumen extending therethrough, a first end comprising the patient puncture tip, a second end comprising the non-patient puncture tip, and an opening through the cannula into the lumen at a location between the first end and the second end providing fluid communication between the lumen of the cannula and the first chamber of the housing.

13. The needle assembly of claim 11, further comprising a first cannula extending from the housing and comprising the patient puncture tip, and a second cannula extending from the housing and comprising the non-patient puncture tip, the first cannula and the second cannula being substantially axially aligned within said housing interior and separated from each other by a gap in fluid communication with the first chamber of the housing.

14. The needle assembly of claim 11, further comprising a sealable sleeve extending about the non-patient puncture tip.

* * * * *